United States Patent
Knight et al.

(10) Patent No.: US 12,165,766 B2
(45) Date of Patent: Dec. 10, 2024

(54) AUTO-PROGRAMMING REQUEST REJECTION REDUCTION

(71) Applicant: CareFusion 303, Inc., San Diego, CA (US)

(72) Inventors: Claire Ellen Knight, Arlington, TX (US); Lisa Diggett, Overland Park, KS (US); Michael K. Workman, Carlsbad, CA (US); Evan Chen, San Diego, CA (US)

(73) Assignee: CareFusion 303, Inc., San Diego, CA (US)

( * ) Notice: Subject to any disclaimer, the term of this patent is extended or adjusted under 35 U.S.C. 154(b) by 320 days.

(21) Appl. No.: 17/528,082

(22) Filed: Nov. 16, 2021

(65) Prior Publication Data

US 2022/0157445 A1 May 19, 2022

Related U.S. Application Data

(60) Provisional application No. 63/115,498, filed on Nov. 18, 2020.

(51) Int. Cl.
*G06Q 10/00* (2023.01)
*G16H 40/40* (2018.01)
*G16H 70/40* (2018.01)

(52) U.S. Cl.
CPC ............. *G16H 40/40* (2018.01); *G16H 70/40* (2018.01)

(58) Field of Classification Search
CPC ............................... G16H 40/40; G16H 70/40
See application file for complete search history.

(56) References Cited

U.S. PATENT DOCUMENTS 5,681,285 A  10/1997 Ford et al.
5,713,856 A   2/1998 Eggers et al.
(Continued)

FOREIGN PATENT DOCUMENTS

WO  WO-2014100736 A2  6/2014

OTHER PUBLICATIONS

International Search Report and Written Opinion for Application No. PCT/US2021/059746, dated Mar. 11, 2022, 20 pages.
(Continued)

*Primary Examiner* — Rajesh Khattar
(74) *Attorney, Agent, or Firm* — Morgan, Lewis & Bockius LLP

(57) ABSTRACT

A method includes receiving a request to activate a medical device. Response to receiving the request, the method includes generating an automatic programming request (APR) for programming the medical device, receiving a message indicating that the APR failed to activate the medical device, and obtaining historical programming records (HPR)s. The method includes determining that parameters in the APR correspond to historical parameters, identifying a set of HPRs including a historical parameter value corresponding to a requested parameter value included the APR, and generating a deviation metric indicating a degree of difference between a secondary parameter value included in the APR and a corresponding historical parameter value. The method includes, responsive to a determination that a deviation metric meets a criticality threshold, changing a drug library record associated with the respective set of deviations and providing an indication to review the changed drug library record.

19 Claims, 8 Drawing Sheets

(56) References Cited

U.S. PATENT DOCUMENTS

| | | | |
|---|---|---|---|
| 7,236,936 | B2 | 6/2007 | White et al. |
| 8,219,413 | B2 | 7/2012 | Martinez et al. |
| 2014/0180711 | A1 | 6/2014 | Kamen et al. |
| 2017/0354365 | A1* | 12/2017 | Zhou .................... A61N 1/3987 |
| 2023/0068131 | A1* | 3/2023 | Zhou ................. A61N 1/36585 |

OTHER PUBLICATIONS

Qiu et al., "A survey of machine learning for big data processing", EURASIP Journal Advances in Signal Processing, May 28, 2016, Article No. 67 (2016), https://doi.org/10.1186/s13634-016-0355-x.

* cited by examiner

AUTO-PROGRAMMING REQUEST REJECTION REDUCTION

CROSS-REFERENCE TO RELATED APPLICATIONS

This application claims priority to and is a non-provisional of U.S. Provisional Application Ser. No. 63/115,498, entitled "AUTO-PROGRAMMING REQUEST REJECTION REDUCTION," filed on Nov. 18, 2020, the entirety of which is hereby incorporated by reference.

TECHNICAL FIELD

The present disclosure generally relates to configuring a medical device, and more specifically relates to methods and systems for identifying errors in medical device programming.

BACKGROUND

Typically, clinicians manually program medical device for each patient. The clinicians are responsible for accurately configuring each medical device to provide patients the necessary treatment they need. Manually configuring medical devices for each patient is time consuming and introduces potential risks. For example, clinicians can accidently program the medical devices to operate at unsafe levels, provide a patient with the incorrect dosage of a drug, provide a patient with an incorrect drug strength, and a number of other potential risks. As such, there is a need to accurately and efficiently configure medical devices.

SUMMARY

In accordance with various implementations, a method of programing a medical device is provided. The method includes receiving, from a user interface, a request to activate the medical device for delivery of a fluid. The method includes, in response to receiving the request, generating, using a drug library, an automatic programming request including one or more parameters for programming the medical device and respective values for the one or more parameters; receiving a failure message indicating that the automatic programming request failed to activate the medical device for delivery of the fluid; and obtaining historical programming records associated with the drug library. The failure message identifies a parameter or a parameter value causing the failure. The historical programming records include respective values for one or more historical parameters, and the historical programming records have caused an activation of a medical device. The method also includes determining that the one or more parameters in the automatic programming request correspond to the one or more historical parameters and identifying a set of historical programming records including a historical parameter value corresponding to a requested parameter value included the automated programming request. The method includes generating a deviation metric indicating a degree of difference between a secondary parameter value included in the automated programming request and a corresponding historical parameter value included in the set of historical programming records. The method includes determining whether the deviation metric satisfies a criticality threshold and, in accordance with a determination that the deviation metric satisfies the criticality threshold, changing a drug library record associated with the respective set of deviations and providing an indication to review the changed drug library record to the user that initiated the request. In some implementations, the method includes in accordance with a determination that the deviation metric does not satisfy the criticality threshold, activating the medical device in accordance with the automatic programming request. In some implementations, the method further includes providing the indication to review the changed drug library record to a third party.

In some implementations, a determination that the deviation metric satisfies the criticality threshold is based on the secondary parameter value included in the automated programming request being outside a guardrail of a corresponding historical parameter value included in the set of historical programming records.

In some implementations, the method includes before changing the drug library record associated with the respective set of deviations, generating one or more recommended values for the secondary parameter value included in the automated programming request. The recommended values for the secondary parameter value are based, in part, on a degree of difference between the secondary parameter value included in the automated programming request and the corresponding historical parameter value included in the set of historical programming records. The method further includes providing the one or more recommended values with the indication to review the changed drug library record to the user that initiated the request. In some implementations, the method includes automatically incorporating the recommended values to the changed drug library record for user review.

In some implementations, when a parameter is identified as a cause of the failure, the failure message further identifies a system generating the automatic programming request as a cause of the medical device failing to activate. In some implementations, when a parameter value is identified as a cause of the failure, the failure message further identifies a change in the drug library as a cause of the medical device failing to activate. In some implementations, the failure message further identifies a device state as a cause of the medical device failing to activate.

In some implementations, the set of historical programming records includes programming records that have caused activation of the medical device. In some implementations, the first parameter includes a drug, diluent, and/or drug concentration. In some implementations, the second parameter includes a rate, volume to be infused, and/or duration. In some implementations, the criticality threshold is specific to a drug library or system.

In accordance with various implementations, a method of programing a medical device via a user device is provided. The method includes providing, via a user device, a request to activate a medical device for delivery of a fluid. The method includes, in response to providing the request, receiving a failure message indicating that an automatic programming request generated using a drug library failed to activate the medical device for delivery of the fluid. The failure message identifies a parameter or a parameter value causing the failure. The method includes receiving an indication to review a changed drug library record that includes one or more changed parameters or one or more changed parameter values for the parameter or the parameter value causing the failure and displaying the changed drug library record via the user device. The changed drug library record identifies the one or more changed parameters or changed parameter values within the automatic programming request generated using the drug library. The method further includes providing an input approving the changed drug library record and activating the medical device for delivery of the fluid using the changed drug library record.

In some implementations, the method further includes, before providing an input approving the changed drug library record, adjusting, via the user device, a parameter or parameter value the changed drug library record. The method further includes providing an adjusted parameter or adjusted parameter value to the changed drug library record and responsive to providing the adjusted parameter or adjusted parameter value to the changed drug library record, receiving an indication that the adjusted parameter or adjusted parameter value to the changed drug library record satisfies a criticality threshold. The method further includes activating the medical device for delivery of the fluid using an adjusted changed drug library record. In some implementations, the method includes, before providing an input approving the changed drug library record, adjusting a parameter or parameter value the changed drug library record. The method further includes providing an adjusted parameter or adjusted parameter value to the changed drug library record and responsive to providing the adjusted parameter or adjusted parameter value to the changed drug library record, receiving another failure message indicating that an adjusted changed drug library record failed to activate the medical device for delivery of the fluid. The other failure message identifies another parameter or another parameter value causing the failure. The method also includes receiving an indication to review another changed drug library record that includes one or more additional changed parameters or one or more additional changed parameter values for the other parameter or other parameter value causing the failure and displaying the other changed drug library record via the user device. The other changed drug library record identifies the one or more additional changed parameters or one or more additional changed parameter values within the automatic programming request generated using the drug library. The method further includes providing an input approving the changed drug library record and activating the medical device for delivery of the fluid using the other changed drug library record.

In some implementations, providing the request to activate the medical device for delivery of the fluid includes scanning a patient, medical device, and/or medical order QR code or barcode. In some implementations, displaying the changed drug library record via the user device, includes displaying one or more recommended values for adjusting the changed drug library record. In some implementations, the automatic programming request is further generated based, at least in part, on one or more of drug information, patient information, drug setup information, and medical device information.

According to various implementations, a method for automatically programming a medical device is provided. The method may include receiving, from a user, a treatment request to administer treatment to a patient via the medical device. The method may include, in response to receiving the treatment request generating an automatic programming request including one or more parameters for programming the medical device, and obtaining historical programming records corresponding to respective drug libraries associated with the treatment request. The historical programming records include one or more historical parameters. The method may include determining, based on a comparison of the one or more parameters of the automatic programming request with corresponding historical parameters of the historical programming records, one or more deviating parameters. The method may further include identifying, from the one or more deviating parameters, one or more primary parameters for programming the medical device. The method may include generating one or more sets of deviations. Each set of deviations is based on a subset of the one or more primary parameters, the subset corresponding to a respective primary parameter. The method may include determining at least one secondary parameter that contributed to one or more deviating parameters of a respective set of deviations. The method may include generating a criticality metric based, in part, on the respective set of deviations and the at least one secondary parameter. The criticality metric defines the overall deviation between the respective set of deviations of the automatic programming request and the historical programming records. The method may further include determining whether the criticality metric meets a criticality threshold, and, in accordance with a determination that the criticality metric meets the criticality threshold, changing a drug library record associated with the respective set of deviations. The method may also include providing an indication to review the changed drug library record to the user that initiated the treatment request.

In some implementations, generating the criticality metric includes determining a deviation magnitude between the at least one secondary parameter and a respective historical parameter of the historical programming records. In some implementations, generating the criticality metric includes determining a size of the respective set of deviations. In some implementations, the criticality metric is based on at least two sets of deviations.

In some implementations, determining the at least one secondary parameter that contributed to the one or more deviating parameters of a respective set of deviations includes identifying a disconnect between the at least one secondary parameter and a respective guardrail of the drug library record associated with the respective set of deviations. In some implementations, the first parameter includes a drug, diluent, and/or drug concentration. In some implementations, the second parameter includes a rate, volume to be infused, and/or duration. In some implementations, the medical device is an infusion pump.

In some implementations, the method may further include, before providing the indication to review the updated drug library record, generating a recommended value for the at least one secondary parameter based, in part, on a deviation magnitude between the at least one secondary parameter and a respective historical parameter of the historical programming records. The method may further include providing the indication to review the updated drug library record and the recommended value for the second parameter to the user. In some implementations, the recommended value for the at least one secondary parameter is automatically incorporated in the updated drug library record.

In some implementations, the criticality threshold is specific to a drug library or system. In some implementations, the method may further include, in accordance with a determination that the criticality metric satisfies the criticality threshold, programming the medical device in accordance with the automatic programming request.

A method of automatically programing a medical device may include providing, via a user device, a treatment request to treat a patient associated with the medical device. The treatment request includes one or more of drug information, patient information, and drug setup information. The method may further include, in response to providing the treatment request, receiving, at a user device, the indication to review an updated drug library record associated with the treatment request. The method may further include, responsive to the indication to review the updated drug library record, displaying the updated library record. The updated drug library record includes one or more parameters that deviated from historical programming records associated with the updated drug library record. The one or more parameters that deviated from historical programming records are based, in part, on one or more of the drug information, patient information, and drug setup information. The method may further include providing input adjusting the one or more parameters. The method may include, responsive to the input, adjusting the one or more parameters, and programming the medical device based on the updated drug library record and the adjusted one or more request parameters.

In some implementations, providing the treatment request includes providing a medical order. The medical orders include a pharmacy order or hospital order. In some implementations, the treatment request includes scanning a patient and/or medical device QR code or barcode. In some implementations, providing the treatment request includes providing medical device information, and the one or more parameters that deviated from historical programming records are based, in part, on the medical device information.

In some implementations, displaying the updated library record for user review includes displaying one or more recommended adjustments to the one or more request parameters.

Other aspects include corresponding systems, apparatuses, and computer program products for implementation of the computer-implemented method.

Further aspects of the subject technology, features, and advantages, as well as the structure and operation of various aspects of the subject technology are described in detail below with reference to accompanying drawings.

DESCRIPTION OF THE FIGURES

Various objects, features, and advantages of the present disclosure can be more fully appreciated with reference to the following detailed description when considered in connection with the following drawings, in which like reference numerals identify like elements. The following drawings are for the purpose of illustration only and are not intended to be limiting of this disclosure, the scope of which is set forth in the claims that follow.

DESCRIPTION

Reference will now be made to implementations, examples of which are illustrated in the accompanying drawings. In the following description, numerous specific details are set forth in order to provide an understanding of the various described implementations. However, it will be apparent to one of ordinary skill in the art that the various described implementations may be practiced without these specific details. In other instances, well-known methods, procedures, components, circuits, and networks have not been described in detail so as not to unnecessarily obscure aspects of the implementations.

The subject technology includes a system and method for automatically programming a medical device. In particular, the subject technology includes a system and method for configuring a medical device based on received treatment requests (e.g., pharmacy orders and/or other hospital orders). An existing point-of-care unit may constantly generate errors when it is incorrectly programmed. When a treatment request is received by the system, the system generates automatic programming requests (APR)s to program a medical device such that the medical device safely administers treatment to a patient. More specifically, the system configures a medical device to administer treatment to a patient as specified in request. Additionally, the system identifies any deviations between the treatment request and historic programming records. The identified deviations are provided to a user, and the user is able to decide how to fully configure the medical device.

Figure 1:
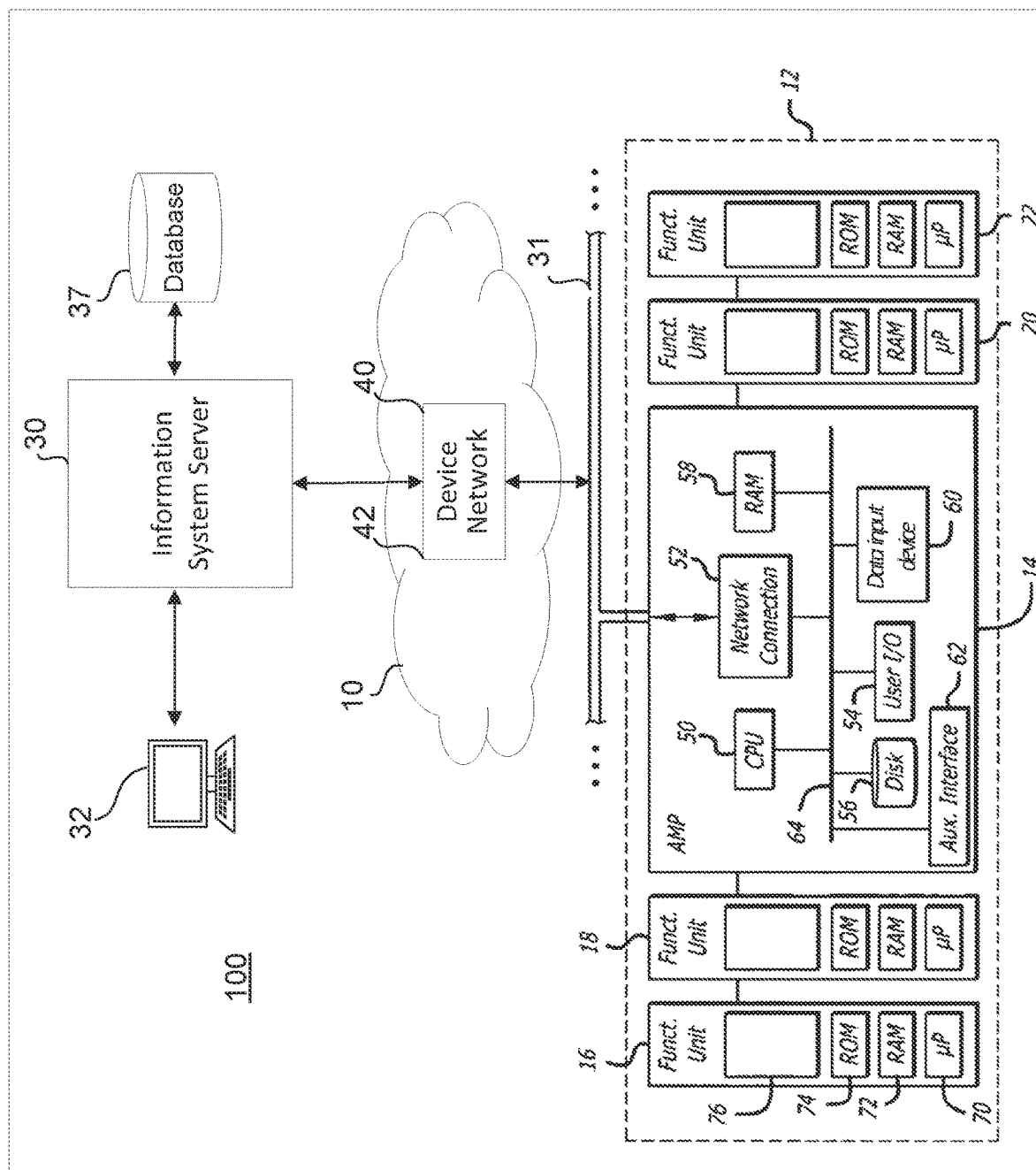
FIG. 1 depicts an example of an institutional patient care system of a healthcare organization, according to various aspects of the subject technology.

FIG. 1 depicts an example of an institutional patient care system 100 of a healthcare organization, according to aspects of the subject technology. In FIG. 1, a patient care device (or "medical device" generally) 12 is connected to a hospital network 10. The term patient care device (or "PCD") may be used interchangeably with the term point-of-care unit (or "PCU"), either which may include various ancillary medical devices such as an infusion pump, a vital signs monitor, a medication dispensing device (e.g., cabinet, tote), a medication preparation device, an automated dispensing device, a module coupled with one of the aforementioned (e.g., a syringe pump module configured to attach to an infusion pump), or other similar devices. Each element 12 is connected to an internal healthcare network 10 by a transmission channel 31. Transmission channel 31 is any wired or wireless transmission channel, for example an 802.11 wireless local area network (LAN). In some implementations, network 10 also includes computer systems located in various departments throughout a hospital. For example, network 10 of FIG. 1 optionally includes computer systems associated with an admissions department, a billing department, a biomedical engineering department, a clinical laboratory, a central supply department, one or more unit station computers and/or a medical decision support system. As described further below, network 10 may include discrete subnetworks. In the depicted example, network 10 includes a device network 40 by which patient care devices 12 (and other devices) communicate in accordance with normal operations.

Additionally, institutional patient care system 100 may incorporate a separate information system server 30, the function of which will be described in more detail below. Moreover, although the information system server 30 is shown as a separate server, the functions and programming of the information system server 30 may be incorporated into another computer, if such is desired by engineers designing the institution's information system. Institutional patient care system 100 may further include one or multiple device terminals 32 for connecting and communicating with information system server 30. Device terminals 32 may include personal computers, personal data assistances, mobile devices such as laptops, tablet computers, augmented reality devices, or smartphones, configured with software for communications with information system server 30 via network 10.

Patient care device 12 comprises a system for providing patient care, such as that described in U.S. Pat. No. 5,713,856 to Eggers et al., which is incorporated herein by reference for that purpose. Patient care device 12 may include or incorporate pumps, physiological monitors (e.g., heart rate, blood pressure, ECG, EEG, pulse oximeter, and other patient monitors), therapy devices, and other drug delivery devices may be utilized according to the teachings set forth herein. In the depicted example, patient care device 12 comprises a control module 14, also referred to as interface unit 14, connected to one or more functional modules 16, 18, 20, 22. Interface unit 14 includes a central processing unit (CPU) 50 connected to a memory, for example, random access memory (RAM) 58, and one or more interface devices such as user interface device 54 (e.g., a display screen and/or keyboard), a coded data input device 60, a network connection 52, and an auxiliary interface 62 for communicating with additional modules or devices. Interface unit 14 also, although not necessarily, includes a main non-volatile storage unit 56, such as a hard disk drive or non-volatile flash memory, for storing software and data and one or more internal buses 64 for interconnecting the aforementioned elements.

In various implementations, user interface device 54 is a touch screen for displaying information to a user and allowing a user to input information by touching defined areas of the screen. Additionally or in the alternative, user interface device 54 could include any means for displaying and inputting information, such as a monitor, a printer, a keyboard, softkeys, a mouse, a track ball and/or a light pen. Data input device 60 may be a bar code reader capable of scanning and interpreting data printed in bar coded format. Additionally or in the alternative, data input device 60 can be any device for entering coded data into a computer, such as a device(s) for reading a magnetic strips, radio-frequency identification (RFID) devices whereby digital data encoded in RFID tags or smart labels (defined below) are captured by the reader 60 via radio waves, PCMCIA smart cards, radio frequency cards, memory sticks, CDs, DVDs, or any other analog or digital storage media. Other examples of data input device 60 include a voice activation or recognition device or a portable personal data assistant (PDA). Depending upon the types of interface devices used, user interface device 54 and data input device 60 may be the same device. Although data input device 60 is shown in FIG. 1 to be disposed within interface unit 14, it is recognized that data input device 60 may be integral within pharmacy system 34 or located externally and communicating with pharmacy system 34 through an RS-232 serial interface or any other appropriate communication means. Auxiliary interface 62 may be an RS-232 communications interface, however any other means for communicating with a peripheral device such as a printer, patient monitor, infusion pump or other medical device may be used without departing from the subject technology. Additionally, data input device 60 may be a separate functional module, such as modules 16, 18, 20 and 22, and configured to communicate with controller 14, or any other system on the network, using suitable programming and communication protocols.

Network connection 52 may be a wired or wireless connection, such as by Ethernet, WiFi, BLUETOOTH, an integrated services digital network (ISDN) connection, a digital subscriber line (DSL) modem or a cable modem. Any direct or indirect network connection may be used, including, but not limited to a telephone modem, an MIB system, an RS232 interface, an auxiliary interface, an optical link, an infrared link, a radio frequency link, a microwave link or a WLANS connection or other wireless connection.

Functional modules 16, 18, 20, 22 are any devices for providing care to a patient or for monitoring patient condition. As shown in FIG. 1, at least one of functional modules 16, 18, 20, 22 may be an infusion pump module such as an intravenous infusion pump for delivering medication or other fluid to a patient. For the purposes of this discussion, functional module 16 is an infusion pump module. Each of functional modules 18, 20, 22 may be any patient treatment or monitoring device including, but not limited to, an infusion pump, a syringe pump, a PCA pump, an epidural pump, an enteral pump, a blood pressure monitor, a pulse oximeter, an EKG monitor, an EEG monitor, a heart rate monitor or an intracranial pressure monitor or the like. Functional module 18, 20 and/or 22 may be a printer, scanner, bar code reader or any other peripheral input, output or input/output device.

Each functional module 16, 18, 20, 22 communicates directly or indirectly with interface unit 14, with interface unit 14 providing overall monitoring and control of device 12. Functional modules 16, 18, 20, 22 may be connected physically and electronically in serial fashion to one or both ends of interface unit 14 as shown in FIG. 1, or as detailed in Eggers et al. However, it is recognized that there are other means for connecting functional modules with the interface unit that may be utilized without departing from the subject technology. It will also be appreciated that devices such as pumps or patient monitoring devices that provide sufficient programmability and connectivity may be capable of operating as stand-alone devices and may communicate directly with the network without connected through a separate interface unit or control unit 14. As described above, additional medical devices or peripheral devices may be connected to patient care device 12 through one or more auxiliary interfaces 62.

Each functional module 16, 18, 20, 22 may include module-specific components 76, a microprocessor 70, a volatile memory 72 and a nonvolatile memory 74 for storing information. It should be noted that while four functional modules are shown in FIG. 1, any number of devices may be connected directly or indirectly to central controller 14. The number and type of functional modules described herein are intended to be illustrative, and in no way limit the scope of the subject technology. Module-specific components 76 include any components necessary for operation of a particular module, such as a pumping mechanism for infusion pump module 16.

While each functional module may be capable of a least some level of independent operation, interface unit 14 monitors and controls overall operation of device 12. For example, as will be described in more detail below, interface unit 14 provides programming instructions to the functional modules 16, 18, 20, 22 and monitors the status of each module.

Patient care device 12 is capable of operating in several different modes, or personalities, with each personality defined by a configuration database. Each mode or personality may include a different set of configuration parameters, or implement a different drug library, as described below. The configuration database may be a database 56 internal to patient care device, or an external database 37. A particular configuration database (or portion thereof) may be selected based, at least in part, by patient-specific information such as patient location, age, physical characteristics, or medical characteristics. Medical characteristics include, but are not limited to, patient diagnosis, treatment prescription, medical history, medical records, patient care provider identification, physiological characteristics or psychological characteristics. As used herein, patient-specific information also includes care provider information (e.g., physician identification) or a patient care device's 10 location in the hospital or hospital computer network. Patient care information may be entered through interface device 52, 54, 60 or 62, and may originate from anywhere in network 10, such as, for example, from a pharmacy server, admissions server, laboratory server, and the like.

A controller 14 of patient care device 12 also has access to a drug library. Further information on drug libraries is contained in U.S. Pat. No. 5,681,285 to Ford, which is incorporated herein by reference in its entirety. The drug library may be resident in the controller, in a local accessible memory, or may be located elsewhere on the system network but be accessible by the controller. "Drug Library Profiles" may be established in which medications (e.g., drugs), concentrations, and other pumping parameters are set particular to that care area—such as, for example, an ICU (intensive care unit) profile, a pediatric profile, a neonatal profile and others. Data sets of medications allowed for use and configurations of pumping parameters including limitations for that use may be available for each drug library profile. As such, drug library profiles may, although not necessarily, correspond to different patient care areas of the hospital. Thus a controller 14 located in a pediatric ward, for example, may utilize a pediatric drug library profile that includes sets of allowed medications, pumping parameters, and pumping limitations that are specific to patients classified as pediatric or located in a pediatric ward. Similarly, a controller 14 located in an ICU may utilize an ICU drug library profile that includes a different set of allowed medications, pumping parameters, and pumping limitations that are specific to patients located in an intensive care environment and other patients requiring intensive care Medical devices incorporating aspects of the subject technology may be equipped with a Network Interface Module (NIM), allowing the medical device to participate as a node in a network. While for purposes of clarity the subject technology will be described as operating in an Ethernet network environment using the Internet Protocol (IP), it is understood that concepts of the subject technology are equally applicable in other network environments, and such environments are intended to be within the scope of the subject technology.

Data to and from the various data sources can be converted into network-compatible data with existing technology, and movement of the information between the medical device and network can be accomplished by a variety of means. For example, patient care device 12 and network 10 may communicate via automated interaction, manual interaction or a combination of both automated and manual interaction. Automated interaction may be continuous or intermittent and may occur through direct network connection 54 (as shown in FIG. 1), or through RS232 links, MIB systems, RF links such as BLUETOOTH, IR links, WLANS, digital cable systems, telephone modems or other wired or wireless communication means. Manual interaction between patient care device 12 and network 10 involves physically transferring, intermittently or periodically, data between systems using, for example, user interface device 54, coded data input device 60, bar codes, computer disks, portable data assistants, memory cards, or any other media for storing data. The communication means in various aspects is bidirectional with access to data from as many points of the distributed data sources as possible. Decision-making can occur at a variety of places within network 10. For example, and not by way of limitation, decisions can be made in HIS server 30, decision support 48, remote data server 49, hospital department or unit stations 46, or within patient care device 12 itself.

All direct communications with medical devices operating on a network in accordance with the subject technology may be performed through information system server 30, known as the remote data server (RDS). In accordance with aspects of the subject technology, network interface modules incorporated into medical devices such as, for example, infusion pumps or vital signs measurement devices, ignore all network traffic that does not originate from an authenticated RDS. The primary responsibilities of the RDS of the subject technology are to track the location and status of all networked medical devices that have NIMs, and maintain open communication.

Figure 2:
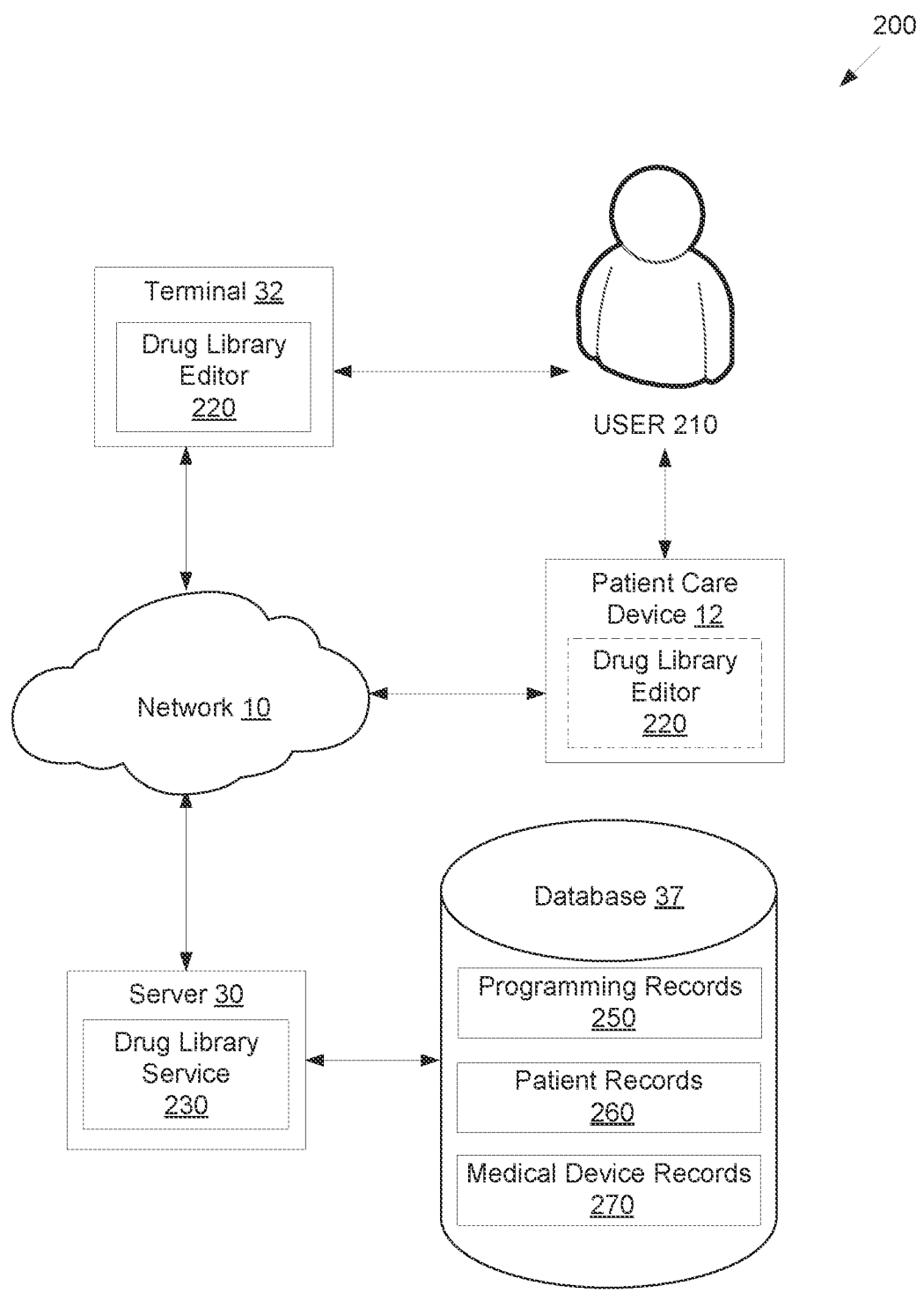
FIG. 2 illustrates an auto-programming system, according to various aspects of the subject technology.

FIG. 2 illustrates an auto-programming system 200 in accordance with some implementations. The auto-programming system 200 includes a device terminal 32, patient care unit 12, network 10, server 30, and external database 37. The device terminal 32, PCU 12, and server 30 are communicatively coupled via the network 10. A user 210 interacts with the device terminal 32 to access a drug library editor (DLE) 220. The DLE 220 allows the user 210 to initiate one or more APRs to program one or more PCUs 12 as discussed below in reference to FIGS. 3A and 3B. Alternative or additionally, in some implementations, the user 210 accesses the DLE 220 directly from the PCU 12. In some implementations, the user 210 includes nurses, clinicians, hospital technicians, and/or other medical practitioners.

An APR includes one or more parameters corresponding to drug information, patient information, and/or drug setup information. The APR configures a PCU 12 such that is operational (or near operational) before or while a patient is being prepared for treatment. In some implementations, the APR is based on prescribed medications, pharmacy orders, and/or other hospital orders. In some implementations, the APR is a based on medical device information, such as a PCU 12 type, version number, functional modules 16, 18, 20, 22, and/or other medical devices being used to treat a patient. For example, in some implementations, the APR is based on the treatments provided to a patient via the one or more functional modules 16, 18, 20, 22 of the PCU 12, and the medical device information specifies the functional modules that are in use, available, and/or the functional modules current application. Additionally or alternatively, in some implementations, the user 210 specifies a particular functional module to provide treatment. In some implementations, the drug information includes one or more drug types, fluids (e.g., diluent), clinical advisories, therapy types (e.g., chemotherapy), drug concentrations, aliases for the drug and/or or fluid, and/or other relevant drug information. In some implementations, the patient information includes a patient's illness and/or disease, allergies, previously administered drugs, current medication, current drug treatments, age, sex, weight, and/or other patient medical history. In some implementations, the drug setup information includes care type, setup for the drug, setup for the fluid, setup for the therapy, setup for an infusion, and/or setup for the drug concentration.

The user 210 provides the drug information, patient information, drug setup information, and/or the medical device information via the device terminal 32 and/or the PCU 12. In some implementations, the drug information, patient information, drug setup information, and/or the medical device information is provided by a user 210 at a remote location (e.g., at a pharmacy). In some implementations, the drug information, patient information, and/or drug setup information is retrieved from prescribed medications, pharmacy orders, and/or other hospital orders provided by the user 210. In some implementations, the user 210 manually provides the patient information and/or medical device information via a device terminal 32 and/or a PCU 12 (e.g., user interface device 54). Alternatively or additionally, in some implementations, the user 210 provides the patient information and/or medical device information by scanning patient and/or medical device QR codes, bar codes, UIDs, and/or other identifiers. The scanned QR codes, bar codes, UIDs, and/or other identifiers that can be decoded or looked up for the relevant patient information and/or medical device information.

In some implementations, the server 30 includes a drug library service 230. The drub library service 230 provides access to the external database 37, which includes one or more programming records 250, patient records 260, and/or medical device records 270.

The one or more programming records 250 include previous configurations of one or more drug library records that were used to (successfully) program a PCU 12. In some implementations, the drug library service 230 maintains a history of programming records 250. The one or more program records 250 include information corresponding to drug library parameters such as a type of drug or fluid, clinical advisories, type of therapy, drug concentrations, aliases for the drug or fluid, care type, setup for the drug or fluid, setup for the therapy, setup for the infusion, and/or setup for the drug concentration. The patient records 260 include patient information as described above. More specifically, the patient records 260 include a patient's medical history, as well as the patient's most current information and other personal information. The medical device records 270 include medical device information as described above. More specifically, the medical device records 270 include information corresponding to the a hospital and/or clinic's medical devices (e.g., PUC's and functional modules 16, 18, 20, 22). For example, the medical device records 270 may indicate that a PCU 12 includes (or operates) as an infusion pump, and/or which functional module is operating as an infusion pump.

The drug library service 230 obtains one or more programming records 250 and compares one or more APRs with the programming records 250 in the external database 37. In particular, the drug library service 230 determines one or more one or more deviations between the APR(s) and one or more programming records 250. A deviation is an APR failure and/or APRs that are overridden to basic programs. A non-exhaustive list of deviations includes one or more ranges in the APR do not match guardrails (e.g., a range or min/max thresholds of a medical device and/or hospital or clinic), drug identified in the APR cannot be found, drug dose unit does not match dose unit in the programming records 250. For example, a drug may not be found because of spelling differences between the user request and programming records 250, unrecognized aliases, specific concentration is not defined in the programming records 250, etc.

In some implementations, the drug library service 230 may identify one or more parameters in an APR that should be stored in the programming records 250, and include the one or more parameters in future programming records 250. For example, the drug library service 230 may identify a concentration that should be stored in the programming records 250 (e.g., a drug concentration that was once rare, but has become prevalent and thus warrants an entry in the programming records 250), and include the concentration in future programming records 250.

The drug library service 230 accesses the external database 37 to obtain relevant patient information and/or medical device information. For instance, drug library service 230 may look up a patient's patient record 260 to retrieve patient information. In some implementations, the patient records 260 are used to configure a PCU 12 based on a patient's medical history, prescribed drugs, and/or other patient information described above. Additionally or alternatively, in some implementations, the patient records 260 are used to determine one or more deviations between the APR(s) and one or more programming records 250. For example, a patient record 260 may indicate that a patient is currently being treated with a first drug. If the first drug reacts in an adverse manner when a second drug is administered to the patient, and the user 210 attempts to administer the second drug to the patient, the drug library service 230 may identify a deviation between the APR(s) and the programming records 250. Similarly, in some implementations, the drug library service 230 may look up a medical device record 270 to retrieve medical device information (e.g., PCU 12 information). In some implementations, the medical device records 270 are used to configure a PCU 12 based on the medical device information. Additionally or alternatively, in some implementations, the medical device records 270 are used to determine one or more one or more deviations between the APR(s) and one or more programming records 250. For example, a medical device record 270 may indicate that a medical device is currently administering a first drug to a patient, if the user 210 attempts to administer the first drug to the patient a second time, the drug library service 230 may identify a deviation between the APR(s) and the programming records 250.

As discussed below, the drug library service 230 updates a drug library record and provides the user 210, via the device terminal 32 and/or PCU 12, an indication to review the updated drug library record. More specifically, an updated drug library record identifies one or more deviations between the one or more APRs and the programming records 250 and provides the user 210 the identified deviations. Alternatively or additionally, in some implementations, before providing the indication to review the updated drug library record, the drug library service 230 generates recommended values for updating the drug library records and provides the user 210 the indication to review the updated drug library record and the recommended values. In yet other implementations, the drug library service 230 generates recommended values for updating the drug library records and incorporates the recommended values in the updated drug library record (which a user 210 still has to review).

Figure 3A:
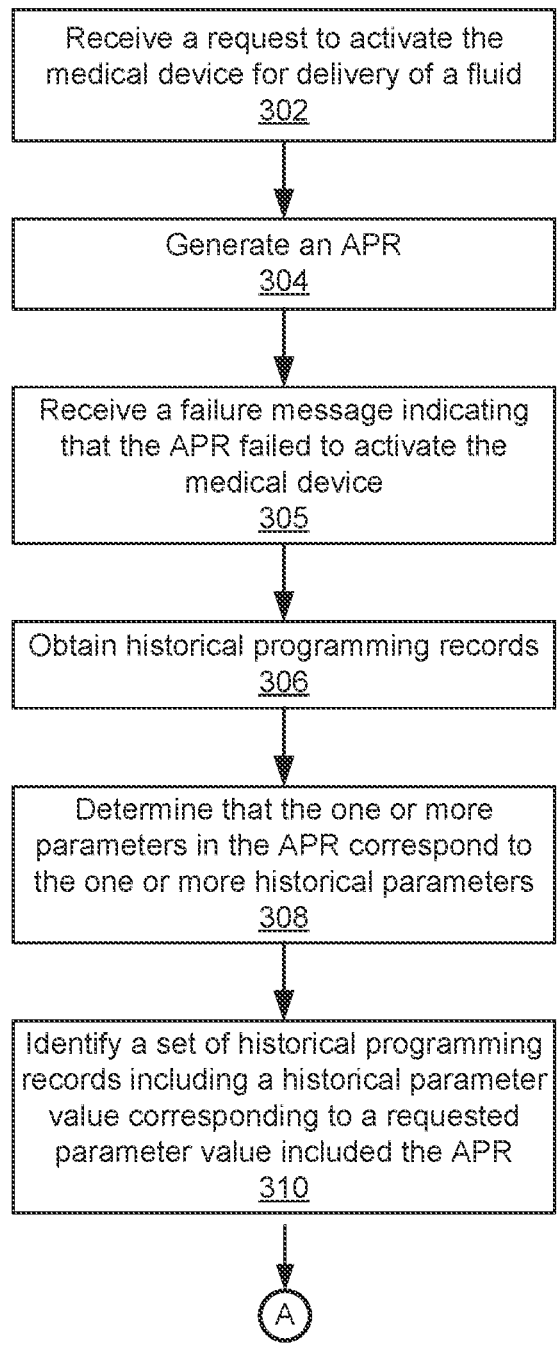
FIGS. 3A and 3B illustrate different operations of an auto-programming system, according to various aspects of the subject technology.
Figure 3B:
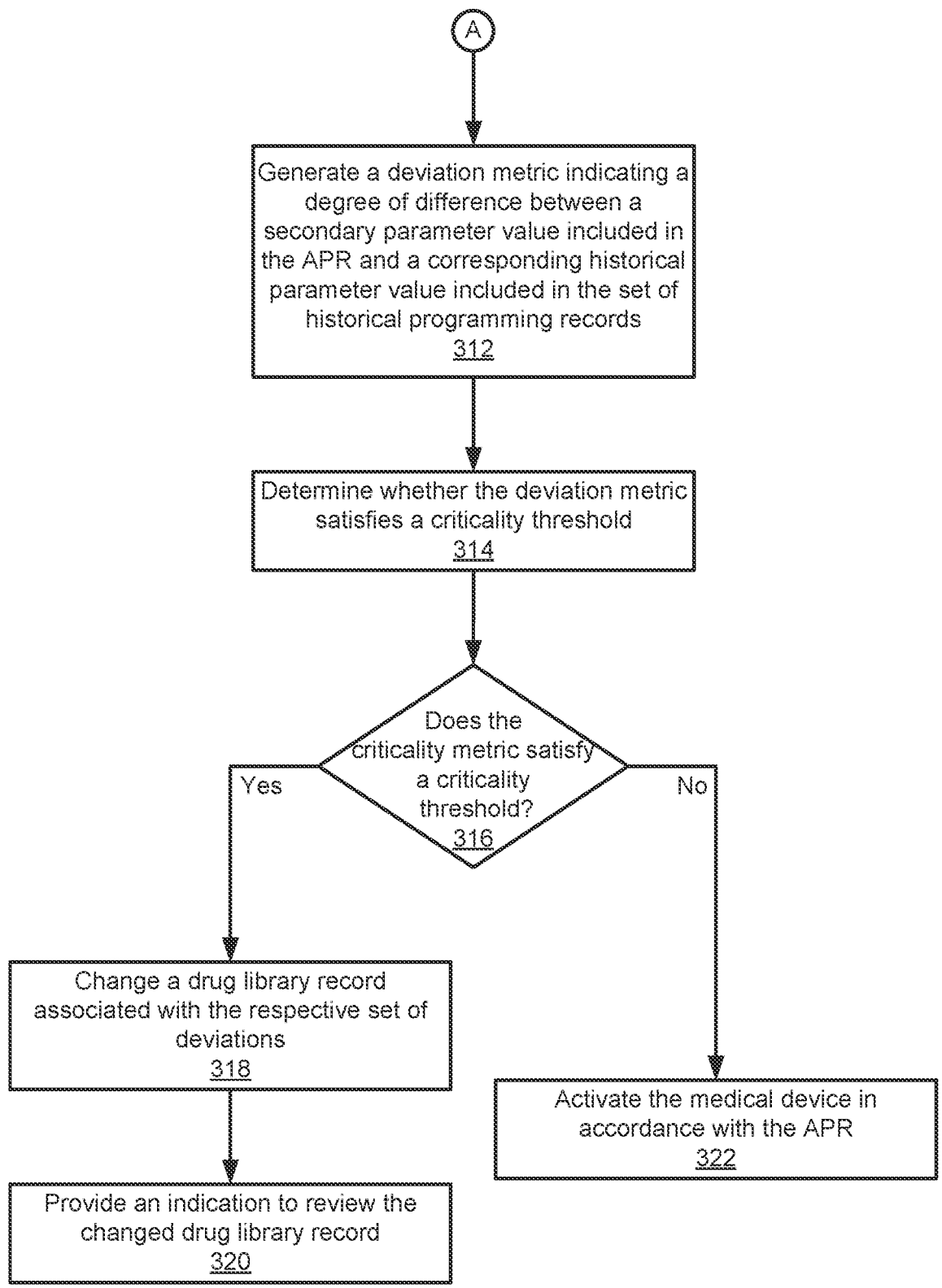

FIGS. 3A and 3B illustrate different operations of an auto-programming system performed by a PCU and/or server, in accordance with some implementations. At least some of the operations are performed by a computer having a processor executing commands stored in a memory of the computer (e.g., CPU 50, and database 56; FIG. 1). In some implementations, information is transmitted between one or more devices in a system (e.g., server 30 and PCU 12; FIG. 1), such as sensor data, stored data, and/or user input information. The operations of the PCU 12 and/or server 30 consistent with the present disclosure may include at least some, but not all, of the operations illustrated in FIGS. 3A and 3B, performed in a different sequence. Similarly, one or more operations illustrated in FIGS. 3A and 3B may be optional. Furthermore, the operations of the PCU 12 and/or server 30 consistent with the present disclosure may include at least two or more steps as in FIGS. 3A and 3B performed overlapping in time, or almost simultaneously. For brevity, the examples provided below are performed at a server 30.

FIGS. 3A and 3B illustrate a process for dynamically programming a system configuring, in accordance with some implementations. The server 30 receives 302, from a user 210 (FIG. 2), e.g., via a user interface, a request to activate a medical device for delivery of a fluid. In some implementations, the request to activate the medical device is identified and/or included in pharmacy orders, prescribed medications, and/or other hospital orders. For example, in some implementations, the server 30 receives from a user 210 a pharmacy order and/or patient information to provide a patient with infusion therapy. In some implementations, the request to activate the medical device includes drug information, patient information, and/or drug setup information. Additionally or alternatively, in some implementations, the request to activate the medical device for delivery of the fluid includes medical device information.

The server 30, in response to receiving the request, generates 304, using a drug library, an APR including one or more parameters for programming the medical device and respective values for the one or more parameters. More specifically, the server 30 retrieves, from the request, drug information, patient information, and/or drug setup information, and generates an APR that includes one or more parameters for programming the medical device (e.g., a PCU 12) and respective values for the one or more parameters based, at least in part, on the retrieved information and a drug library. In some implementations, the server 30 retrieves from the request to activate the medical device medical device information. For example, the server 30 may retrieve from a pharmacy order a drug type and/or a drug concentration, and generate an APR including parameters corresponding to the drug type and/or drug concentration identified by the pharmacy order and/or patient information. The different parameters of an APR are discussed above in reference to FIG. 2.

In some implementations, the server 30, in response to receiving the request, receives 305 a failure message indicating that the APR failed to activate the medical device. The failure message identifies a parameter or a parameter value causing the failure. In some implementations, the failure message includes one or more failure conditions, such as a deviation in the parameters (also referred to as primary parameters, e.g., a therapy type), a deviation in parameter values (also referred to as secondary parameters, e.g., an infusion rate), and/or device state failures (e.g., air in line, device in idle state, etc.). In some implementations, the failure message identifies a potential cause of the failure. For example, if a deviation in the parameters is determined, a failure message may identify a change in a configuration of a system (e.g., server 30) generating the APR as a potential cause of a failure condition. In some implementations, if a deviation in the parameter values is determined, a failure message may identify a change in a drug library as a potential cause of a failure condition (e.g., increased guardrail warnings). Examples of the device state failures are provided below. In some implementations, the primary parameters include one or more drug types, fluid types, clinical advisories, therapy types, drug concentrations, and/or aliases for the drug or fluid. In some implementations, the secondary parameters include care types, drug setups, fluid setups, therapy setup, infusion setup, and/or drug concentration setup. Examples of the secondary parameters include an infusion rate, volume to be infused (VTBI), and/or duration.

The server 30, in response to receiving the request, further obtains 306 historical programming records associated with the drug library. The historical programming records include one or more records in programming records 250 in the external database 37. The historical programming records include respective values for one or more historical parameters. In particular, the historical programming records include one or more parameters and parameter values that have been used to successfully program the medical device with a drug library record (i.e., the historical programming records are programming records that have caused an activation of a medical device). In some implementations, the server 30 obtains patient records 260 and/or medical device records 270. The patient records 260 and/or medical device records 270 include one or more parameters that have been used to successfully program the medical device with the drug library record.

The server 30 determines (308) that the one or more parameters in the APR correspond to the one or more historical parameters, identifies (310) a set of historical programming records including a historical parameter value corresponding to a requested parameter value included in the APR. In particular, the server 30 identifies one or more parameters and/or parameter values of the APR and respective parameters and/or parameter values that are included in the set of historical programming records. In some implementations, the server 30 identifies a set of historical programming records by comparing one or more parameters and/or parameter values of the APR with the one or more respective parameters and/or parameter values of the set of historical programming records (e.g., programming records 250). For example, a primary parameter included in the APR may be pain management therapy and the server 30 identifies a set of historical programming records including a historical parameter for pain management therapy. For example, a secondary parameter value included in the APR may be heparin and the server 30 identifies a set of historical programming records including a historical parameter value of heparin. As another example, a secondary parameter value included in the APR may be a drug dose unit and the server 30 identifies a set of historical programming records including a historical parameter value of the drug dose unit.

In some implementations, the server 30 determines whether there is at least one common secondary parameter value included in the APR and a corresponding historical parameter value included in the set of historical programming records. For example, a secondary parameter value included in the APR can have a first infusion rate (where the APR is identified as having a primary parameter of a first drug type, therapy type etc.) and a historical parameter value included in a set of historical programming records (e.g., one or more programming records 250) can also have the first infusion rate. Similarly, in some implementations, the server 30 determines whether there is at least one deviation in a secondary parameter value included in the APR and a corresponding historical parameter value included in the set of historical programming records. For example, the server 30 can determine that a VTBI value (e.g., a secondary parameter value) included in an APR for a first therapy type (e.g., chemotherapy) is distinct from a historic VTBI value identified in a set of historical programming records. In some implementations, the server 30 determines that there is a disconnect between at least one secondary parameter and a respective historical parameter value in the set of historical programming records. A disconnect, in accordance with some implementations, is a deviation between a secondary parameter and a respective historical parameter value that is outside a guardrail included in the set of historical programming records for the drug library (e.g., the drug library used to generate the APR).

The server 30 generates (312) a deviation metric indicating a degree of difference between a secondary parameter value included in the APR and a corresponding historical parameter value included in the set of historical programming records. For example, the secondary parameter value included in the APR may define a VTBI of 100 ml and the historical parameter value included in the historical programming records may define an average VTBI of 75 ml, and the deviation metric generated by the server may indicate a degree of difference between the VTBIs (e.g., 25 ml). In another example, the secondary parameter value included in the APR may define a drug dose unit (e.g., ml) and the historical parameter value included in the historical programming records may define a distinct drug dose unit (e.g., oz), and the deviation metric generated by the server may indicate a degree of difference between ml and ozs. In some implementations, the server 30 may identify a difference between a secondary parameter value included in the APR and a corresponding historical parameter value included in the set of historical programming records but determine that there is no degree of difference. For example, the secondary parameter value included in the APR may define a drug order with a strength of 1000 mg/100 m, but a corresponding historical parameter value included in the set of historical programming records may have a strength of 1 Gm/100 mL, and the deviation metric generated by the server may indicate that the values are equal. In some implementations, a deviation metric is generated for each secondary parameter value included in the APR that deviates from a corresponding historical parameter value included in the set of historical programming records. In some implementations, the server 30 compares patient records 250 and/or medical device records 270 with the APR to determine additional deviations.

In some implementations, the server 30 generates a deviation metric indicating a degree of difference between primary parameters in the APR and corresponding primary parameters in the set of historical programming records and/or a degree of difference between secondary parameters in the APR and corresponding secondary parameters in the set of historical programming records. In some implementations, the server 30 generates a deviation metric indicating a difference between a current device state and an expected device state (e.g., program secondary without primary or when in idle state; bolus without running infusion; secondary arrives before primary (e.g., before order, or before transmitted); syringe, etc.). Additional examples of the one or more deviations are provided above in FIG. 2.

In some implementations, the server 30 identifying differences between one or more parameters and/or parameter values of the APR and respective parameters and/or parameter values of the historical programming records includes identifying error types (or other failure conditions). For example, the server 30 may identify an increase in a total number of specific error types over time. As another example, the server 30 may identify an increase in errors (or specific error types) for a specific drug, specific medical device, specific medical device configuration (e.g., firmware version, configuration version, etc.), or the like. A non-exhaustive list of error types includes a system error, system offline, noncompliant parameters, nonmatching parameters, invalid step, and/or system busy. The error types can be associated with specific errors. For example, the system error can have specific errors such as "APR file name invalid" and/or "APR file failed to open;" the system offline can have specific errors such as "channel offline" (where a channel is a functional module 16, 18, 20, 22 as described above in FIG. 1), the noncompliant parameters can have specific errors such as "missing info," "invalid info," parameter "over system limit," parameter "under system limit," parameters "over_ct_limit" ("ct" stands for channel), and/or parameters "under_ct_limit;" nonmatching parameters can have specific errors such as "not found drug lib," "not found ct lib," and/or "channel prog mismatch." The invalid step error type can have specific errors such as "titrate idle channel," "bolus idle channel," "bolus unsupported," "secondary idle channel," and/or "secondary unsupported;" the system busy error type can have specific errors such as "basic executing," "bolus executing," "secondary executing," "PCU alarm state," "channel alarm state," "PCU programming state," "channel programming state," and/or other programming state. The innovative features monitors these errors and error types over time and can proactively adjust the system to reduce the occurrence of the errors, in some cases, before an end user is aware of a misconfiguration.

The server 30 further determines 314 whether the deviation metric satisfies a criticality threshold. In some implementations, the criticality threshold is specific to a drug library (e.g., for a drug library used to generate the APR). Alternatively or additionally, in some implementations, the criticality threshold is specific to a hospital and/or clinic system. In some implementations, the criticality threshold is predetermined degree of difference from a historical parameter value (e.g., +/−5% from a historical parameter value, +/−10% from a historical parameter value). For example, a historical parameter value included in a historical programming records may be an average VTBI of 75 ml, and the criticality threshold may be a VTBI of 78.75 ml or greater and/or a VTBI of 71.25 ml or less (e.g., +/−5% from the average VTBI of 75 ml). Alternative, in some implementations, the criticality threshold is a predetermined value and the criticality threshold is satisfied when the difference between a second parameter value and an average historical parameter value is greater than the criticality threshold. In some implementations, the criticality threshold is based on a guardrail included in the set of historical programming records for the drug library.

In accordance with a determination that the deviation metric satisfies 316 the criticality threshold ("yes" at step 316), the server 30 changes 318 a drug library record associated with the respective set of deviations and provides 320 an indication to review the changed drug library record to the user 210 (e.g., via a user interface) that initiated the request. In particular, the server 30 changes one or more secondary parameter values included in the APR for a drug library and provides the user 210 an indication of the APR faults and/or failures (and their respective changes). In this way, the user 210 can easily identify the one or more parameters that were adjusted (if any). In some implementations, before changing a drug library record associated with the respective set of deviations, the server 30 generates one or more recommended values (if any) for the at least one secondary parameter based, in part, on a degree of difference between a secondary parameter value included in the APR and a corresponding historical parameter value included in the set of historical programming records and provides the one or more recommended values with the indication to review the changes to a drug library record to the user 210. In some implementations, the server 30 automatically incorporates the recommended values to the changed drug library record for user review.

In some implementations, the server 30 may transmit a message regarding the failure to a third-party, such as the device manufacturer. For example, if the device is connected with another system (e.g., electronic medical records system) that may have changed its configuration, the device may experience an increased incidence of failures. This may be due to a change in how the connected system provides a parameter, parameter value, or other information to the device. In this way, the third-party may proactively identify configuration failures before a serious adverse event occurs. In some implementations, the third-party system may initiate deployment of updated software to address the condition. In some implementations, the third-party system may transmit a suggested configuration update to a device management server associated with sites having devices that may be susceptible to the failure. In some implementations, the third-party system ay transmit a suggested configuration update to the electronic medical records system indicating that the potential change has negatively impacted the device(s).

The features may provide an early warning to device users. For example, the failure may be associated with a specific parameter that is not frequently used across one or more clinics. Upon detection of the failure from a first site, the third-party server may identify an inconsistency and alert other sites of a potential inconsistency with their configuration.

In some implementations, the APR faults and/or failures include one or more reject types. The one or more reject types may include system offline, parameters noncompliant, parameters nonmatching, invalid step, busy at this time. In some implementations, the one or more reject types include a description, likely cause, and/or resolution. For example, a reject type for system offline can have a description indicating "unable to communicate to device or channel," provide a likely cause of "wireless network," and/or provide a resolution such as "first look for wifi signal and then call tech support" A reject type for parameters noncompliant can have a description indicating "the message is malformed, missing or parameter is outside of the allowable range," provide a likely cause of "Auto Program request protocol isn't being followed," and/or provide a resolution such as "call tech support and report error and details of order." A reject type for parameters nonmatching can have a description indicating "unable to match requested drug to the profile and/or running channel," provide a likely cause of "drug is not in the drug library for the profile, order doesn't match an already running channel, or scanning wrong device (ex. volumetric pump vs. syringe pump vs. patient controlled analgesic pump)," and/or provide a resolution such as "first check device for correct channel and care area and then call drug library admin." A reject type for invalid step, can have a description indicating "a match was found, but the infusion step is not supported on the channel," provide a likely cause of "possible issue with order or existing drug configuration (e.g., running primary doesn't support piggyback)," and/or provide a resolution such as "first check device for correct channel and clinical workflow and then either call drug library admin or prescriber." A reject type for busy at this time can have a description indicating "a match was found and infusion is executable but the PCU or channel is currently in use," provide a likely cause of "the system is alarming, the channel is in the act of being programmed, or the channel is running an unsupported infusion step," and/or provide a resolution such as "clear device of alarms or programming conditions then allow running step to complete to scan again." The APR faults and/or failures may include reject types, descriptions, likely causes, and/or resolutions no described above.

Alternatively, in accordance with a determination that the deviation metric does not satisfy 316 the criticality threshold ("no" at step 316), the server 30 activates the medical device in accordance with the APR (e.g., the medical device is activated without changes to the drug library record).

Figure 4A:
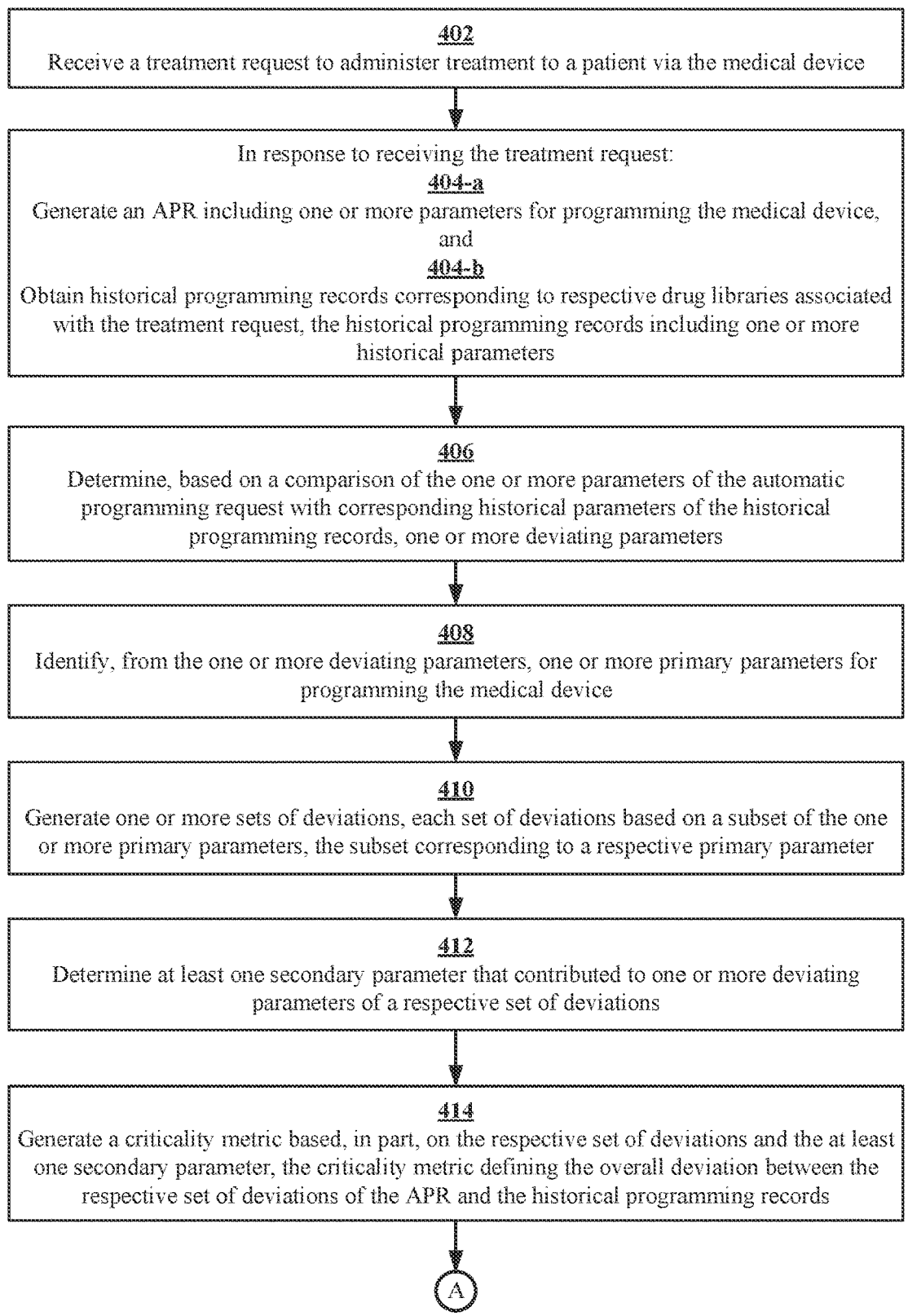
FIGS. 4A and 4B is a flowchart illustrating a method for automatically programing a medical device, according to various aspects of the subject technology.
Figure 4B:
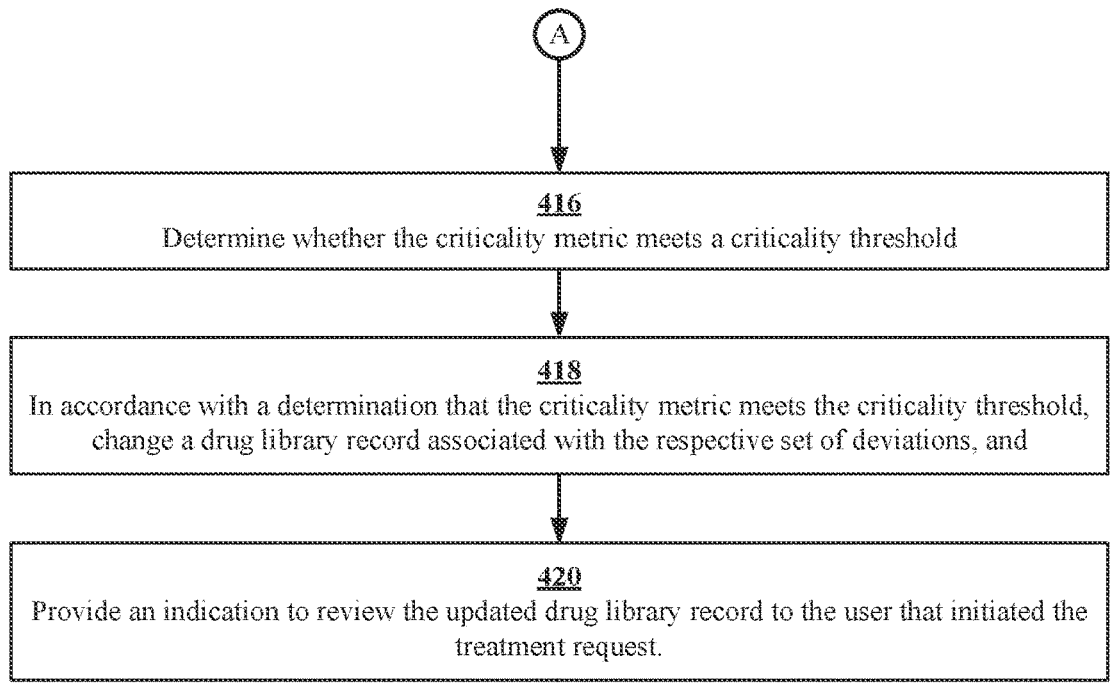
Figure 5:
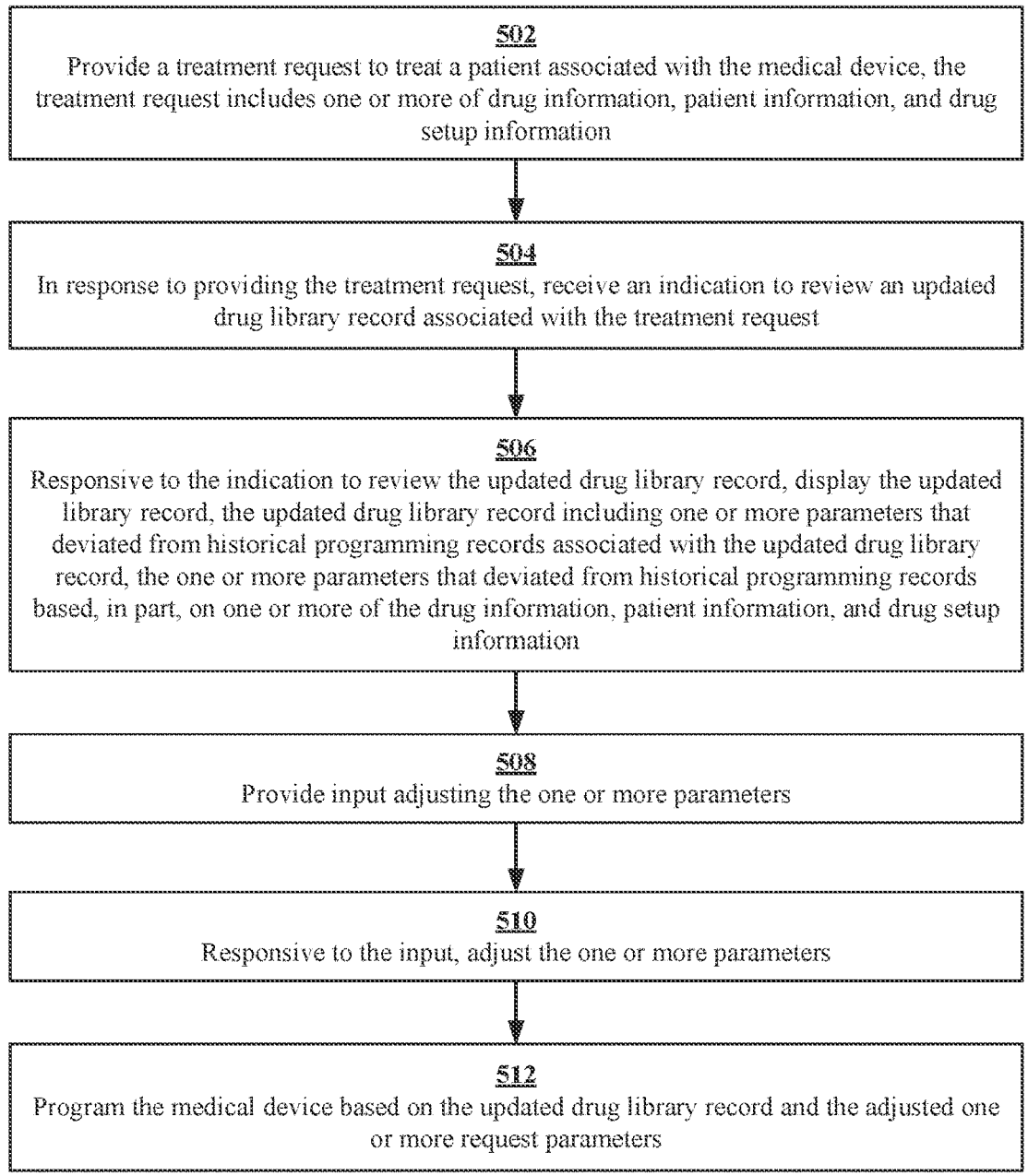
FIG. 5 is a flowchart illustrating a method for initiating an automatic programming of a medical device, according to various aspects of the subject technology.

FIGS. 4A-5 are flowcharts illustrating a method of automatically programing a medical device according to some implementations. The operations described in FIGS. 4 and 5 may be performed at one or more device terminals, patient care units 12, and/or server 30. More specifically, the operations described in FIGS. 4 and 5 are performed by a computer having a processor executing commands stored in a memory of the computer (e.g., CPU 50, and database 56). In some implementations, information is transmitted between one or more devices in a system (e.g., server 30 and PCUs 12), such as drug information, drug setup information, patient information, and/or medical device information. The operations described in FIGS. 4 and 5 may include at least some, but not all, of the operations illustrated in FIGS. 4 and 5, performed in a different sequence. Similarly, one or more operations illustrated in FIGS. 4 and 5 may be optional. Furthermore, the operations described in FIGS. 4 and 5 may include at least two or more steps performed overlapping in time, or almost simultaneously.

Method 400 illustrates a method of generating APRs for programing a medical device, in accordance with some implementations. For brevity, method 400 is described as being performed by a server 30 (FIG. 1). The method 400 includes receiving (402), from a user 210, a treatment request to administer treatment to a patient via a medical device (e.g., a PCU 12). The treatment request can include drug information, patient information, and/or drug setup information (similar to the user requests described above in FIGS. 2-3B). Additionally or alternatively, in some implementations, the treatment request includes prescribed medications, pharmacy orders, and/or other hospital orders.

The method 400 includes, in response to receiving the treatment request, generating (404-*a*) an APR including one or more parameters for programming the medical device, and obtaining (404-*b*) historical programming records corresponding to respective drug libraries associated with the treatment request. The historical programming records include one or more historical parameters. The APR is based, in part, on the treatment request to program a medical device. More specifically, the APR includes one or more parameters based on drug information, patient information, and/or drug setup information included in the treatment request. In some implementations, the server 30 retrieves (e.g., extracts) information from prescribed medications, pharmacy orders, and/or other hospital orders to define one or more parameters of the APR. The server 30 obtains the historical programming records for an external database 37 (e.g., programming records 250; FIG. 2). In some implementations, the server 30 obtains patient records 260 and/or medical device records 270 (from external database 37) to define one or more parameters of the APR. Alternatively or additionally, in some implementations, the server 30 obtains the patient records 260 and/or medical device records 270 to use in conjunction with the programming records 250.

The method 400 includes determining (406), based on a comparison of the one or more parameters of the automatic programming request with corresponding historical parameters of the historical programming records, one or more deviating parameters. For example, as described above in reference to FIGS. 3A and 3B, the server 30 identifies one or more deviations between one or more parameters and/or one or more parameter values of the APR and one or more respective parameters and/or one or more respective parameter values of the programming records 250. The method 400 further includes identifying (408), from the one or more deviating parameters, one or more primary parameters for programming the medical device. The primary parameters are described above in reference to FIGS. 3A-3B. For example, as described above, a primary parameter can be a drug type, and a deviation can be different spellings of the drug name. The method 400 includes generating (410) one or more sets of deviations. Each set of deviations is based on a subset of the one or more primary parameters, the subset corresponding to a respective primary parameter. In some implementations, each set of deviations is associated with a respective drug library record. In other words, each set of deviations is based on a primary parameter and includes one or more historic programming records (e.g., programming records 250) that deviate from an APR based on the primary parameter. For example, a first set of deviations can include one or more historic programing records that have a different spelling than the spelling of the drug included in the APR drug type parameter (i.e., a primary parameter).

The method 400 includes determining (412) at least one secondary parameter that contributed to one or more deviating parameters of a respective set of deviations. The secondary parameters are described above in reference to FIGS. 3A and 3B. For example, the APR can include a parameter corresponding to a rate at which a drug is to be infused, and the server 30 can determine that the rate is a secondary parameter based on a comparison of the rate defined in the APR with corresponding rates in one or more historic programming records of a set of deviations (corresponding to the same drug). In other words, the server 30 can determine that there is a variance between the defined rate in the APR and the rate within the one or more programming records of a set of deviations.

The method 400 includes generating (414) a criticality metric based, in part, on the respective set of deviations and the at least one secondary parameter. The criticality metric defines the overall deviation between the respective set of deviations of the APR and the historical programming records. In some implementations, the criticality metric is based on at least two sets of deviations. Alternatively or additional, in some implementations, the criticality metric is based on a magnitude of deviation between at least one secondary parameter and a respective historical parameter of the historical programming records of the respective set of deviations. For example, continuing the example above, if the rate defined in the APR (i.e., the secondary parameter) is equal (or substantially equal) to the rate defined in the one or more historical programming records of the respective set of deviations, then critically metric will be smaller. Alternatively, if the rate defined in the APR (i.e., the secondary parameter) is substantially smaller or greater than the rate defined in the one or more historical programming records of the respective set of deviations, then critically metric will be larger.

The method 400 further includes determining (416) whether the criticality metric meets a criticality threshold, and, in accordance with a determination that the criticality metric meets the criticality threshold, changing (418) a drug library record associated with the respective set of deviations. More specifically, the server 30 identifies the one or more parameters in the APR that deviate from the drug library record (based on the respective set of deviations of one or more historic programming records). The method 400 includes providing (420) an indication to review the changed drug library record to the user that initiated the treatment request. In this way, the user 210 is provided with the deviations and can take the necessary steps to adjust the APR as needed. In some implementations, the server 30 determines one or more recommended values for the changed drug library record. More specifically, the server 30 provides a user 210 with recommended values to adjust the one or more deviating parameters. By providing recommended values to the one or more deviating parameters, the method 400 allows the user to quickly resolve inconsistencies and errors in the configuration of the medical device. Alternatively or additionally, in some implementations, the server automatically applies the recommended adjustments to the changed drug library record provides the changed drug library record for user review.

Method 500 illustrates a method of providing a request to program a medical device, in accordance with some implementations. For brevity, method 500 is described as being performed by a device terminal 32 (FIG. 1). The method 500 providing (502) a treatment request to treat a patient associated with the medical device (e.g., PCU 12). The treatment request includes one or more of drug information, patient information, and drug setup information. As described above, the treatment request is used to generate one or more parameters for an APR based on one or more of drug information, patient information, and drug setup information. As described above in FIGS. 2 and 3, a user 210 can provide drug information, patient information, and drug setup information by providing one or more orders, such as prescribed medications, pharmacy orders, and/or hospital orders. In some implementations, the user 210 can further provide patient information by manually inputting the patient's information and/or scanning the patient's associated QR code or bar code. In some implementations, the treatment request includes medical device information, and the one or more parameters are further based on the medical device information. In some implementations, the user 210 can provide the medical device information by manually inputting the medical device information and/or scanning the medical device's associated QR code or bar code.

The method 500 includes, in response to providing the treatment request, receiving (504), at a user device, the indication to review an updated drug library record associated with the treatment request. The updated drug library record includes one or more updated parameters that deviated from the one or more parameters based on the treatment request. The updated drug library record is described above in reference to FIGS. 3 and 4. The method 500 includes responsive to the indication to review the updated drug library record, displaying (506) the updated library record. The updated drug library record includes one or more parameters that deviated from historical programming records associated with the updated drug library record. The one or more parameters that deviated from historical programming records are based, in part, on one or more of the drug information, patient information, and drug setup information. As mentioned above, the user 210 is provided with the one or more deviations between the drug library record and the APR. In this way, the user 210 is able to review the deviations and changes as needed. In some implementations, the method 500 further includes displaying one or more recommended adjustment parameters. The one or more recommended adjustment parameters are provided to the user 210 to allow them to quickly resolve inconsistencies and errors in the programming of the medical device.

The method 500 includes providing (508) input adjusting the one or more parameters, and, in response to receiving the input, adjusting (510) the one or more parameters based on the input. The method 500 further includes programming (512) the medical device based on the updated drug library record and the adjusted one or more request parameters.

Figure 6:
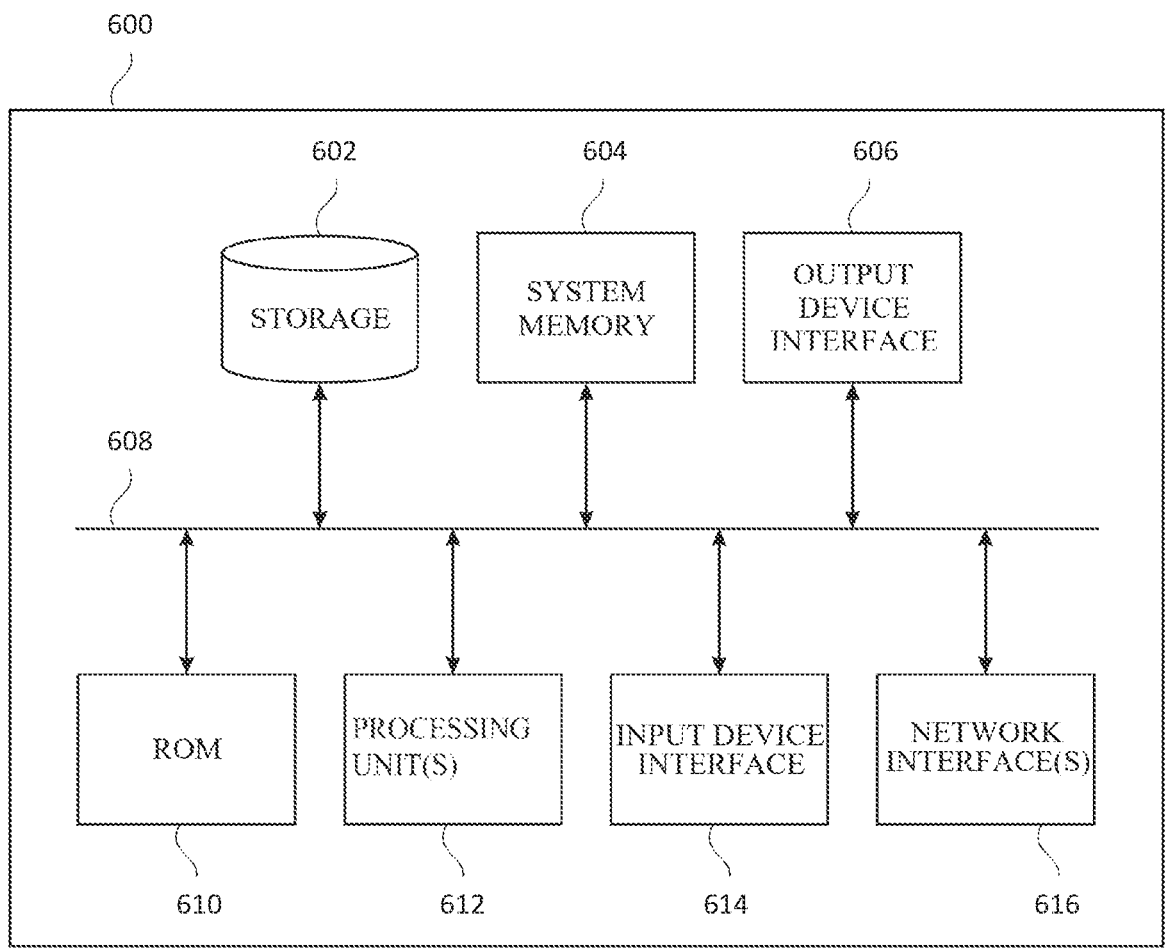
FIG. 6 is a conceptual diagram illustrating an example electronic system for implementing an auto-programming system, according to various aspects of the subject technology.

FIG. 6 is a conceptual diagram illustrating an example electronic system 600 for implementing a DLE 220, according to various aspects of the subject technology. Electronic system 600 may be a computing device for execution of software associated with one or more operations or steps of FIGS. 3A and 3B, or components and processes provided by FIGS. 3A-5. Electronic system 600 may be representative, in combination with the disclosure regarding FIGS. 1-5, of the DLE 220 described above. In this regard, electronic system 600 may be a microcomputer, personal computer or a mobile device such as a smartphone, tablet computer, laptop, PDA, an augmented reality device, a wearable such as a watch or band or glasses, or combination thereof, or other touch screen or television with one or more processors embedded therein or coupled thereto, or any other sort of computer-related electronic device having network connectivity.

Electronic system 600 may include various types of computer readable media and interfaces for various other types of computer readable media. In the depicted example, electronic system 600 includes a bus 608, processing unit(s) 612, a system memory 604, a read-only memory (ROM) 610, a permanent storage device 602, an input device interface 614, an output device interface 606, and one or more network interfaces 616. In some implementations, electronic system 600 may include or be integrated with other computing devices or circuitry for operation of the various components and processes previously described.

Bus 608 collectively represents all system, peripheral, and chipset buses that communicatively connect the numerous internal devices of electronic system 600. For instance, bus 608 communicatively connects processing unit(s) 612 with ROM 610, system memory 604, and permanent storage device 602.

From these various memory units, processing unit(s) 612 retrieves instructions to execute and data to process in order to execute the processes of the subject disclosure. The processing unit(s) can be a single processor or a multi-core processor in different implementations.

ROM 610 stores static data and instructions that are needed by processing unit(s) 612 and other modules of the electronic system. Permanent storage device 602, on the other hand, is a read-and-write memory device. This device is a non-volatile memory unit that stores instructions and data even when electronic system 600 is off. Some implementations of the subject disclosure use a mass-storage device (such as a magnetic or optical disk and its corresponding disk drive) as permanent storage device 602.

Some implementations use a removable storage device (such as a floppy disk, flash drive, and its corresponding disk drive) as permanent storage device 602. Like permanent storage device 602, system memory 604 is a read-and-write memory device. However, unlike storage device 602, system memory 604 is a volatile read-and-write memory, such as a random access memory. System memory 604 stores some of the instructions and data that the processor needs at runtime.

In some implementations, the processes of the subject disclosure are stored in system memory 604, permanent storage device 602, and/or ROM 610. From these various memory units, processing unit(s) 612 retrieves instructions to execute and data to process in order to execute the processes of some implementations.

Bus 608 also connects to input and output device interfaces 614 and 606. Input device interface 614 enables the user to communicate information and select commands to the electronic system. Input devices used with input device interface 614 include, e.g., alphanumeric keyboards and pointing devices (also called "cursor control devices"). Output device interfaces 606 enables, e.g., the display of images generated by the electronic system 600. Output devices used with output device interface 606 include, e.g., printers and display devices, such as cathode ray tubes (CRT) or liquid crystal displays (LCD). Some implementations include devices such as a touchscreen that functions as both input and output devices.

Also, bus 608 also couples electronic system 600 to a network (not shown) through network interfaces 616. Network interfaces 616 may include, e.g., a wireless access point (e.g., Bluetooth or WiFi) or radio circuitry for connecting to a wireless access point. Network interfaces 616 may also include hardware (e.g., Ethernet hardware) for connecting the computer to a part of a network of computers such as a local area network ("LAN"), a wide area network ("WAN"), wireless LAN, or an Intranet, or a network of networks, such as the Internet. Any or all components of electronic system 600 can be used in conjunction with the subject disclosure.

These functions described above can be implemented in computer software, firmware or hardware. The techniques can be implemented using one or more computer program products. Programmable processors and computers can be included in or packaged as mobile devices. The processes and logic flows can be performed by one or more programmable processors and by one or more programmable logic circuitry. General and special purpose computing devices and storage devices can be interconnected through communication networks.

Some implementations include electronic components, such as microprocessors, storage and memory that store computer program instructions in a machine-readable or computer-readable medium (alternatively referred to as computer-readable storage media, machine-readable media, or machine-readable storage media). Some examples of such computer-readable media include RAM, ROM, read-only compact discs (CD-ROM), recordable compact discs (CD-R), rewritable compact discs (CD-RW), read-only digital versatile discs (e.g., DVD-ROM, dual-layer DVD-ROM), a variety of recordable/rewritable DVDs (e.g., DVD-RAM, DVD-RW, DVD+RW, etc.), flash memory (e.g., SD cards, mini-SD cards, micro-SD cards, etc.), magnetic and/or solid state hard drives, read-only and recordable Blu-Ray® discs, ultra density optical discs, any other optical or magnetic media, and floppy disks. The computer-readable media can store a computer program that is executable by at least one processing unit and includes sets of instructions for performing various operations. Examples of computer programs or computer code include machine code, such as is produced by a compiler, and files including higher-level code that are executed by a computer, an electronic component, or a microprocessor using an interpreter.

While the above discussion primarily refers to microprocessor or multi-core processors that execute software, some implementations are performed by one or more integrated circuits, such as application specific integrated circuits (ASICs) or field programmable gate arrays (FPGAs). In some implementations, such integrated circuits execute instructions that are stored on the circuit itself.

As used in this specification and any claims of this application, the terms "computer," "server," "processor," and "memory" all refer to electronic or other technological devices. These terms exclude people or groups of people. For the purposes of the specification, the terms display or displaying means displaying on an electronic device. As used in this specification and any claims of this application, the terms "computer readable medium" and "computer readable media" are entirely restricted to tangible, physical objects that store information in a form that is readable by a computer. These terms exclude any wireless signals, wired download signals, and any other ephemeral signals.

To provide for interaction with a user, implementations of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; e.g., feedback provided to the user can be any form of sensory feedback, e.g., visual feedback, audible feedback, or tactile feedback; and input from the user can be received in any form, including acoustic, speech, or tactile input. In addition, a computer can interact with a user by sending documents to and receiving documents from a device that is used by the user; e.g., by sending web pages to a web browser on a user's client device in response to requests received from the web browser.

Implementations of the subject matter described in this specification can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the subject matter described in this specification, or any combination of one or more such back end, middleware, or front end components. The components of the system can be interconnected by any form or medium of digital data communication, e.g., a communication network. Examples of communication networks include a local area network ("LAN") and a wide area network ("WAN"), an internetwork (e.g., the Internet), and peer-to-peer networks (e.g., ad hoc peer-to-peer networks).

The computing system can include clients and servers. A client and server are generally remote from each other and may interact through a communication network. The relationship of client and server arises by virtue of computer programs running on the respective computers and having a client-server relationship to each other. In some implementations, a server transmits data (e.g., an HTML page) to a client device (e.g., for purposes of displaying data to and receiving user input from a user interacting with the client device). Data generated at the client device (e.g., a result of the user interaction) can be received from the client device at the server.

Those of skill in the art would appreciate that the various illustrative blocks, modules, elements, components, methods, and algorithms described herein may be implemented as electronic hardware, computer software, or combinations of both. To illustrate this interchangeability of hardware and software, various illustrative blocks, modules, elements, components, methods, and algorithms have been described above generally in terms of their functionality. Whether such functionality is implemented as hardware or software depends upon the particular application and design constraints imposed on the overall system. Skilled artisans may implement the described functionality in varying ways for each particular application. Various components and blocks may be arranged differently (e.g., arranged in a different order, or partitioned in a different way) all without departing from the scope of the subject technology.

It is understood that the specific order or hierarchy of steps in the processes disclosed is an illustration of example approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

The previous description is provided to enable any person skilled in the art to practice the various aspects described herein. The previous description provides various examples of the subject technology, and the subject technology is not limited to these examples. Various modifications to these aspects will be readily apparent to those skilled in the art, and the generic principles defined herein may be applied to other aspects. Thus, the claims are not intended to be limited to the aspects shown herein, but is to be accorded the full scope consistent with the language claims, wherein reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit this disclosure.

The term website, as used herein, may include any aspect of a website, including one or more web pages, one or more servers used to host or store web related content, etc. Accordingly, the term website may be used interchangeably with the terms web page and server. The predicate words "configured to," "operable to," and "programmed to" do not imply any particular tangible or intangible modification of a subject, but, rather, are intended to be used interchangeably. For example, a processor configured to monitor and control an operation or a component may also mean the processor being programmed to monitor and control the operation or the processor being operable to monitor and control the operation. Likewise, a processor configured to execute code can be construed as a processor programmed to execute code or operable to execute code.

The term automatic, as used herein, may include performance by a computer or machine without user intervention; for example, by instructions responsive to a predicate action by the computer or machine or other initiation mechanism. The word "example" is used herein to mean "serving as an example or illustration." Any aspect or design described herein as "example" is not necessarily to be construed as preferred or advantageous over other aspects or designs.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "implementation" does not imply that such implementation is essential to the subject technology or that such implementation applies to all configurations of the subject technology. A disclosure relating to an implementation may apply to all implementations, or one or more implementations. An implementation may provide one or more examples. A phrase such as an "implementation" may refer to one or more implementations and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such as a "configuration" may refer to one or more configurations and vice versa.

As used herein, the terms "determine" or "determining" encompass a wide variety of actions. For example, "determining" may include calculating, computing, processing, deriving, generating, obtaining, looking up (e.g., looking up in a table, a database or another data structure), ascertaining and the like via a hardware element without user intervention. Also, "determining" may include receiving (e.g., receiving information), accessing (e.g., accessing data in a memory) and the like via a hardware element without user intervention. "Determining" may include resolving, selecting, choosing, establishing, and the like via a hardware element without user intervention.

As used herein, the terms "provide" or "providing" encompass a wide variety of actions. For example, "providing" may include storing a value in a location of a storage device for subsequent retrieval, transmitting a value directly to the recipient via at least one wired or wireless communication medium, transmitting or storing a reference to a value, and the like. "Providing" may also include encoding, decoding, encrypting, decrypting, validating, verifying, and the like via a hardware element.

As used herein, the term "message" encompasses a wide variety of formats for communicating (e.g., transmitting or receiving) information. A message may include a machine readable aggregation of information such as an XML document, fixed field message, comma separated message, or the like. A message may, in some implementations, include a signal utilized to transmit one or more representations of the information. While recited in the singular, it will be understood that a message may be composed, transmitted, stored, received, etc. in multiple parts.

As used herein, the term "selectively" or "selective" may encompass a wide variety of actions. For example, a "selective" process may include determining one option from multiple options. A "selective" process may include one or more of: dynamically determined inputs, preconfigured inputs, or user-initiated inputs for making the determination. In some implementations, an n-input switch may be included to provide selective functionality where n is the number of inputs used to make the selection.

As used herein, the terms "correspond" or "corresponding" encompasses a structural, functional, quantitative and/or qualitative correlation or relationship between two or more objects, data sets, information and/or the like, preferably where the correspondence or relationship may be used to translate one or more of the two or more objects, data sets, information and/or the like so to appear to be the same or equal. Correspondence may be assessed using one or more of a threshold, a value range, fuzzy logic, pattern matching, a machine learning assessment model, or combinations thereof.

In any implementation, data generated or detected can be forwarded to a "remote" device or location, where "remote," means a location or device other than the location or device at which the program is executed. For example, a remote location could be another location (e.g., office, lab, etc.) in the same city, another location in a different city, another location in a different state, another location in a different country, etc. As such, when one item is indicated as being "remote" from another, what is meant is that the two items can be in the same room but separated, or at least in different rooms or different buildings, and can be at least one mile, ten miles, or at least one hundred miles apart. "Communicating" information references transmitting the data representing that information as electrical signals over a suitable communication channel (e.g., a private or public network). "Forwarding" an item refers to any means of getting that item from one location to the next, whether by physically transporting that item or otherwise (where that is possible) and includes, at least in the case of data, physically transporting a medium carrying the data or communicating the data. Examples of communicating media include radio or infra-red transmission channels as well as a network connection to another computer or networked device, and the internet or including email transmissions and information recorded on websites and the like.

Aspects described include artificial intelligence or other operations whereby the system processes inputs and generates outputs with apparent intelligence. The artificial intelligence may be implemented in whole or in part by a model. A model may be implemented as a machine learning model. The learning may be supervised, unsupervised, reinforced, or a hybrid learning whereby multiple learning techniques are employed to generate the model. The learning may be performed as part of training. Training the model may include obtaining a set of training data and adjusting characteristics of the model to obtain a desired model output. For example, three characteristics may be associated with a desired item location. In such instance, the training may include receiving the three characteristics as inputs to the model and adjusting the characteristics of the model such that for each set of three characteristics, the output device state matches the desired device state associated with the historical data.

In some implementations, the training may be dynamic. For example, the system may update the model using a set of events. The detectable properties from the events may be used to adjust the model.

The model may be an equation, artificial neural network, recurrent neural network, convolutional neural network, decision tree, or other machine-readable artificial intelligence structure. The characteristics of the structure available for adjusting during training may vary based on the model selected. For example, if a neural network is the selected model, characteristics may include input elements, network layers, node density, node activation thresholds, weights between nodes, input or output value weights, or the like. If the model is implemented as an equation (e.g., regression), the characteristics may include weights for the input parameters, thresholds or limits for evaluating an output value, or criterion for selecting from a set of equations.

Once a model is trained, retraining may be included to refine or update the model to reflect additional data or specific operational conditions. The retraining may be based on one or more signals detected by a device described herein or as part of a method described herein. Upon detection of the designated signals, the system may activate a training process to adjust the model as described.

Further examples of machine learning and modeling features which may be included in the implementations discussed above are described in "A survey of machine learning for big data processing" by Qiu et al. in EURASIP Journal on Advances in Signal Processing (2016) which is hereby incorporated by reference in its entirety.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for." Furthermore, to the extent that the term "include," "have," or the like is used in the description or the claims, such term is intended to be inclusive in a manner similar to the term "comprise" as "comprise" is interpreted when employed as a transitional word in a claim.

What is claimed is:

1. A method of programing a medical device, comprising, at a server:
   receiving, from a user device communicatively coupled with the server, a request to activate the medical device for delivery of a fluid, the request including patient information and at least one of drug information, medical device information, and drug setup information;
   in response to receiving the request:
      generating, using a drug library stored in a database communicatively coupled with the server, an automatic programming request including one or more parameters for programming the medical device and respective values for the one or more parameters, wherein the one or more parameters and the respective values for the one or more parameters are based on the request,
      receiving a failure message indicating that the automatic programming request failed to activate the medical device for delivery of the fluid, wherein the failure message identifies a deviating parameter associated with a failure of the automatic programming request, and
      obtaining historical programming records associated with the drug library and corresponding to the request, the historical programming records including respective values for one or more historical parameters, and wherein the historical programming records caused an activation of the medical device;
   determining that the one or more parameters in the automatic programming request correspond to the one or more historical parameters;
   identifying a set of historical programming records including a historical parameter value corresponding to a requested parameter value included the automated programming request;
   generating a deviation metric indicating a degree of difference between a value of the respective values for the one or more parameters included in the automated programming request and a corresponding historical parameter value included in the set of historical programming records;
   determining whether the deviation metric satisfies a criticality threshold;
   in accordance with a determination that the deviation metric satisfies the criticality threshold:
      changing a drug library record associated with a respective set of deviations including the deviating parameter associated with the failure of the automated programming request, and
      providing, via a user interface of the user device, the changed drug library record to a user that initiated the request; and
   in response to receiving from the communicatively coupled user device input approving the changed drug library record, activating, by the server, the medical device to cause the medical device to deliver the fluid to a patient via an infusion line based on the changed drug library record.

2. The method of claim 1, wherein a determination that the deviation metric satisfies the criticality threshold is based on the value of the respective values for the one or more parameters included in the automated programming request being outside a guardrail of a corresponding historical parameter value included in the set of historical programming records.

3. The method of claim 1, further comprising:
   before changing the drug library record associated with the respective set of deviations, generating one or more recommended values for the value of the respective values for the one or more parameters included in the automated programming request, the recommended values for the value of the respective values for the one or more parameters based, in part, on a degree of difference between the value of the respective values for the one or more parameters included in the automated programming request and the corresponding historical parameter value included in the set of historical programming records; and
   providing the one or more recommended values with an indication to review the changed drug library record to the user that initiated the request.

4. The method of claim 3, further comprising automatically incorporating the recommended values to the changed drug library record for user review.

5. The method of claim 1, wherein, when a parameter is identified as a cause of the failure, the failure message further identifies a system generating the automatic programming request as a cause of the medical device failing to activate.

6. The method of claim 1, wherein, when a parameter value is identified as a cause of the failure, the failure message further identifies a change in the drug library as a cause of the medical device failing to activate.

7. The method of claim 1, wherein the failure message further identifies a device state as a cause of the medical device failing to activate.

8. The method of claim 1, further comprising providing an indication to review an changed drug library record to a third party.

9. The method of claim 1, wherein the set of historical programming records includes programming records that have caused activation of the medical device.

10. The method of claim 1, wherein the one or more parameters includes drug types, fluid types, clinical advisories, therapy types, and/or drug concentrations.

11. The method of claim 1, wherein the respective values of the one or more parameters includes a rate, volume to be infused, and/or duration.

12. The method of claim 1, wherein the criticality threshold is specific to a drug library or system.

13. A method of programing a medical device, comprising:
- providing, via a user device, a request to activate a medical device for delivery of a fluid, the request including patient information and at least one of drug information, medical device information, and drug setup information;
- in response to providing the request, receiving, for display at the user device, a failure message indicating that an automatic programming request generated using a drug library failed to activate the medical device for delivery of the fluid, wherein the failure message identifies a deviating parameter associated with a failure of the automatic programming request;
- receiving a changed drug library record that includes one or more changed parameters or one or more changed parameter values for the deviating parameter or a value of the deviating parameter that is causing the failure;
- displaying the changed drug library record via the user device, wherein the changed drug library record identifies the one or more changed parameters or changed parameter values within the automatic programming request generated using the drug library and based on a respective set of deviations including the deviating parameter associated with the failure of the automatic programming request; and
- in response to an input provided at the user device approving the changed drug library record, activating, via the user device, the medical device for delivery of the fluid to a patient via an infusion line using the changed drug library record.

14. The method of claim 13, further comprising:
- before providing an input approving the changed drug library record, adjusting a parameter or parameter value the changed drug library record;
- providing an adjusted parameter or adjusted parameter value to the changed drug library record;
- responsive to providing the adjusted parameter or adjusted parameter value to the changed drug library record, receiving an indication that the adjusted parameter or adjusted parameter value to the changed drug library record satisfies a criticality threshold; and
- activating the medical device for delivery of the fluid using an adjusted changed drug library record.

15. The method of claim 13, further comprising:
- before providing an input approving the changed drug library record, adjusting a parameter or parameter value the changed drug library record;
- providing an adjusted parameter or adjusted parameter value to the changed drug library record;
- responsive to providing the adjusted parameter or adjusted parameter value to the changed drug library record, receiving another failure message indicating that an adjusted changed drug library record failed to activate the medical device for delivery of the fluid, wherein the other failure message identifies another deviating parameter associated with another failure of the automatic programming request;
- receiving another changed drug library record that includes one or more additional changed parameters or one or more additional changed parameter values for the other deviating parameter or a value of the other deviating parameter that is causing the failure;
- displaying the other changed drug library record via the user device, wherein the other changed drug library record identifies the one or more additional changed parameters or one or more additional changed parameter values within the automatic programming request generated using the drug library and based on another respective set of deviations including the other deviating parameter associated with the other failure of the automatic programming request;
- providing an input approving the changed drug library record; and
- activating the medical device for delivery of the fluid using the other changed drug library record.

16. A method of claim 13, wherein
- the request includes one or more of drug information, patient information, drug setup information, and medical device information; and
- the automatic programming request is further generated based, at least in part, on one or more of the drug information, the patient information, the drug setup information, and the medical device information.

17. The method of claim 13, wherein providing the request to activate the medical device for delivery of the fluid includes scanning a patient, medical device, and/or medical order QR code or barcode.

18. The method of claim 13, wherein displaying the changed drug library record via the user device, includes displaying one or more recommended values for adjusting the changed drug library record.

19. A non-transitory, computer-readable medium storing instructions which, when executed by a processor in a computer, cause the computer to perform a method, the method comprising:
- receiving, from a user device communicatively coupled with a server, a request to activate a medical device for delivery of a fluid, the request including patient information and at least one of drug information, medical device information, and drug setup information;
- in response to receiving the request:
  - generating, using a drug library stored in a database communicatively coupled with the server, an automatic programming request including one or more parameters for programming the medical device and respective values for the one or more parameters, wherein the one or more parameters and the respective values for the one or more parameters are based on the request,
  - receiving a failure message indicating that the automatic programming request failed to activate the medical device for delivery of the fluid, wherein the failure message identifies a deviating parameter associated with a failure of the automatic programming request, and
  - obtaining historical programming records associated with the drug library and corresponding to the request, the historical programming records including respective values for one or more historical parameters, and wherein the historical programming records caused an activation of the medical device;
- determining that the one or more parameters in the automatic programming request correspond to the one or more historical parameters;
- identifying a set of historical programming records including a historical parameter value corresponding to a requested parameter value included the automatic programming request;
- generating a deviation metric indicating a degree of difference between a value of the respective values for the one or more parameters included in the automatic programming request and a corresponding historical parameter value included in the set of historical programming records;
determining whether the deviation metric satisfies a criticality threshold;
in accordance with a determination that the deviation metric satisfies the criticality threshold:
 changing a drug library record associated with a respective set of deviations including the deviating parameter associated with a failure of the automatic programming request, and
 providing, via a user interface of the user device, an indication to review the changed drug library record to a user that initiated the request; and
in response to receiving from the communicatively coupled user device input approving the changed drug library record, activating, by the processor, the medical device to cause the medical device to deliver the fluid to a patient via an infusion line using the changed drug library record.

* * * * *